United States Patent
Chang et al.

(10) Patent No.: US 10,925,572 B1
(45) Date of Patent: Feb. 23, 2021

(54) GEOMETRIC CALIBRATION METHOD AND SYSTEM FOR DUAL AXIS DIGITAL TOMOSYNTHESIS

(71) Applicant: Institute of Nuclear Energy Research, Atomic Energy Council, Executive Yuan, R.O.C, Taoyuan (TW)

(72) Inventors: Chia-Hao Chang, Taoyuan (TW); Sheng-Pin Tseng, Taoyuan (TW); Yu-Ching Ni, Taoyuan (TW); Fan-Pin Tseng, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 0 days.

(21) Appl. No.: 16/795,682

(22) Filed: Feb. 20, 2020

(30) Foreign Application Priority Data

Oct. 30, 2019 (TW) ................................ 10813923.9

(51) Int. Cl.
*A61B 6/04* (2006.01)
*A61B 6/00* (2006.01)

(52) U.S. Cl.
CPC ............ *A61B 6/583* (2013.01); *A61B 6/0492* (2013.01); *A61B 6/5223* (2013.01)

(58) Field of Classification Search
CPC ...... A61B 6/0492; A61B 6/5223; A61B 6/583
See application file for complete search history.

(56) References Cited

U.S. PATENT DOCUMENTS

| | | | | |
|---|---|---|---|---|
| 5,835,563 A | * | 11/1998 | Navab ...................... | A61B 6/12 378/207 |
| 2003/0058999 A1 | * | 3/2003 | Mitschke ............. | G01N 23/046 378/207 |
| 2004/0013240 A1 | * | 1/2004 | Mitschke ............... | A61B 34/20 378/205 |
| 2005/0094771 A1 | * | 5/2005 | Basu ...................... | A61B 6/032 378/207 |
| 2005/0265523 A1 | * | 12/2005 | Strobel ................ | A61B 6/4441 378/193 |

(Continued)

OTHER PUBLICATIONS

Chang, Chia-Hao et al., A geometric calibration method for the digital chest tomosynthesis with dual-axis scanning geometry, Plos One, 2019.

*Primary Examiner* — Mark R Gaworecki
(74) *Attorney, Agent, or Firm* — Locke Lord LLP; Tim Tingkang Xia, Esq.

(57) ABSTRACT

A geometric calibration method for dual-axis digital tomosynthesis includes the steps of: providing a calibration phantom having a first plate, a second plate parallel to the first plate, and mark points distributed to the first and second plates; arranging any mark point at the first plate not to be vertically collinear with a mark point at the second plate; projecting the calibration phantom onto a planar detector to obtain a projected calibration-phantom image; deriving a conversion relationship between the mark point and the corresponding projected position at the planar detector to further establish a projection matrix related to an imaging system; and, applying the projection matrix to calculate a plurality of geometric parameters. In addition, a geometric calibration system for dual-axis digital tomosynthesis is also provided.

5 Claims, 5 Drawing Sheets

(56) References Cited

U.S. PATENT DOCUMENTS

| | | | | |
|---|---|---|---|---|
| 2007/0122020 A1* | 5/2007 | Claus | ............... | A61B 6/583 |
| | | | | 382/131 |
| 2008/0093544 A1* | 4/2008 | Wang | ............... | A61B 6/583 |
| | | | | 250/252.1 |
| 2010/0284601 A1* | 11/2010 | Rubner | ............ | A61B 6/4441 |
| | | | | 382/132 |
| 2014/0205058 A1* | 7/2014 | Tagawa | ............ | G06T 11/005 |
| | | | | 378/11 |
| 2018/0014809 A1* | 1/2018 | Lin | ............... | A61B 6/584 |

* cited by examiner

GEOMETRIC CALIBRATION METHOD AND SYSTEM FOR DUAL AXIS DIGITAL TOMOSYNTHESIS

CROSS REFERENCE TO RELATED APPLICATION

This application claims the benefits of Taiwan application Serial No. 108139239, filed on Oct. 30, 2019, the disclosures of which are incorporated by references herein in its entirety.

TECHNICAL FIELD

The present disclosure relates in general to a geometric calibration method and system for dual-axis digital tomosynthesis.

BACKGROUND

In the art, a conventional digital tomosynthesis (DTS) system has been widely applied as a clinical diagnosis tool in various medical imaging applications such as digital breast tomosynthesis and digital chest tomosynthesis. In a typical imagining process of the DTS, a series of projected images upon an object would be obtained at a limited angle. The conventional DTS systems can provide three-dimensional (3D) image information, comparable to computed tomography (CT), with a lower radiation dose. Nevertheless, imaging quality of a typical chest DTS is generally limited due to its single-axis scan direction from head to feet (hereinafter, H-F direction). In other words, an X-ray source of the conventional DTS is moved along a scan path in the H-F direction defined at the person or object to be examined. Because of phantom effects such as Blurring ripples or Ghost distortions, indistinct imaging parallel to the scan direction would be induced. Namely, in the conventional chest DTS, acceptable quality imaging at some particular portions might not be obtained due to inherent characteristics of the scan direction. At this time, beside the existing H-F scan direction, if an additional scan direction from left to right (hereinafter, L-R direction) can be provided to form a dual-axis imaging scan, then the aforesaid concern at the indistinct imaging would be resolved. Here, the scan in the L-R direction is that the X-ray source of the conventional DTS is moved along a scan path in the L-R direction defined at the person or object to be examined.

Figure 1:
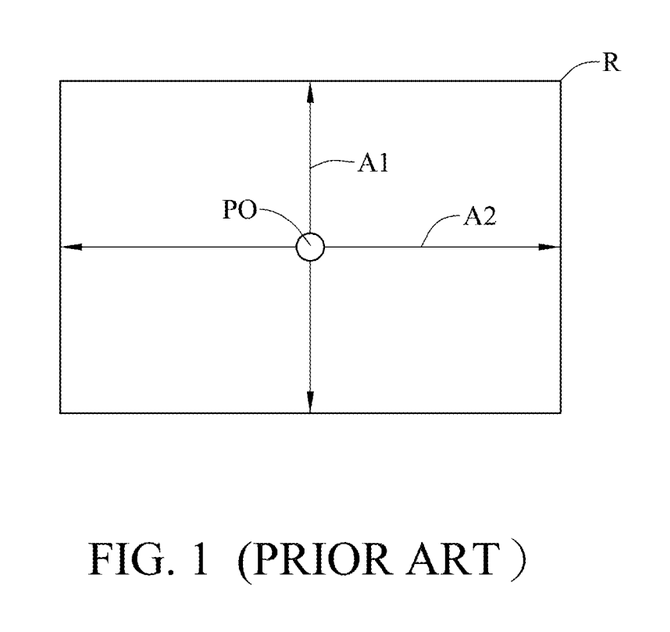
FIG. 1 shows schematically a dual-axis scan in the art.

However, in comparison with the single-axis scan, a kinematic pattern of the dual-axis scan would be highly possibly associated with higher or more complicated geometric misalignments due to its own geometric features of the scan mechanism. For a single-axis scan-geometry mechanism, since the scan direction is only limited to the H-F direction, thus possible kinematic errors can be only presented in an entire off-axial manner without altering geometric relationships over the person or object to be scanned. Namely, in the condition that all the position relationships upon the object to be scanned are fixed, corresponding reconstructed images would only meet an off-axial concern, not a phantom issue. For example, referring to FIG. 1, within a detection range R of a detector for a system having a dual-axis scan geometry, a center point of the H-F directional scan axis A1 and another center point of the L-R directional scan axis A2 (perpendicular to the H-F directional scan axis A1) shall be coincided, say at an overlap position PO. Obviously, scan deviations would occur (1) if the center point of the H-F directional scan axis A1 and the center point of the L-R directional scan axis A2 are not coincided, or (2) if the H-F directional scan axis A1 is not perpendicular to the L-R directional scan axis A2. For a DTS system having a dual-axis scan geometry, any geometric misalignment, axial offset or tilt, would induce artifacts at the reconstructed images.

Thus, an improved geometric calibration method and system for dual-axis digital tomosynthesis to avoid the aforesaid imaging problems is definitely urgent and welcome to the skill in the art.

SUMMARY

An object of the present disclosure is to provide a geometric calibration method and system for dual-axis digital tomosynthesis to reduce possible artifacts caused by dual-axis scan-geometry misalignments.

In one embodiment of this disclosure, a geometric calibration method for dual-axis digital tomosynthesis includes: a step of providing a calibration phantom, wherein the calibration phantom includes a first plate, a second plate and a plurality of mark points, the first plate and the second plate are spaced by a depth distance in a depth direction, and the plurality of mark points is distributed to the first plate and the second plate; a step of, in the depth direction, arranging a 3D coordinate position of any of the plurality of mark points at the first plate not to be collinear with another 3D coordinate position of another one of the plurality of mark points at the second plate; a step of utilizing an X-ray to project the calibration phantom onto a planar detector, so as to obtain a projected calibration-phantom image, wherein the 3D coordinate position of each of the plurality of mark points disposed at the first plate and the second plate is in correspondence to a 2D projected coordinate position at the planar detector; a step of deriving a conversion relationship between the 3D coordinate position of each of the plurality of mark points disposed at the first plate and the second plate and the corresponding 2D projected coordinate position to establish a projection matrix related to an imaging system; and, a step of applying the projection matrix to calculate a plurality of geometric parameters.

In another embodiment of this disclosure, a geometric calibration system for dual-axis digital tomosynthesis includes a planar detector, a light source and a calibration phantom. The light source is used for emitting an X-ray. The geometric calibration phantom includes a first plate, a second plate and a plurality of mark points. The first plate and the second plate are spaced by a depth distance in a depth direction, the plurality of mark points is distributed to the first plate and the second plate, and, in the depth direction, a 3D coordinate position of any of the plurality of mark points at the first plate is not collinear with another 3D coordinate position of another one of the plurality of mark points at the second plate. The calibration phantom is projected onto the planar detector via the X-ray to obtain a projected calibration-phantom image, and the 3D coordinate position of each of the plurality of mark points disposed at the first plate and the second plate is in correspondence to a 2D projected coordinate position at the planar detector. A conversion relationship between the 3D coordinate position of each of the plurality of mark points disposed at the first plate and the second plate and the corresponding 2D projected coordinate position is derived to establish a projection matrix related to an imaging system. The projection matrix is applied to calculate a plurality of geometric parameters.

As stated above, by providing the geometric calibration method and system applicable for the digital tomosynthesis system with dual-axis scan geometry according to this disclosure, the aforesaid shortcoming that the conventional geometric calibration method and apparatus cannot be applied to the imaging system with the dual-axis scan geometry can be substantially resolved. In this disclosure, the geometric calibration method applies basically the projection matrix to utilize position relationships between the calibration-phantom mark points and the corresponding projected mark points to derive the geometric parameters sufficient for representing the digital tomosynthesis system with the dual-axis digital scan geometry.

In addition, in the geometric calibration phantom provided by this disclosure, an interlacing arrangement of the mark points at the first and second plates are specifically applied, such that the digital tomosynthesis system with the dual-axis scan geometry in accordance with this disclosure can resolve the problems in overlapping the related mark points during the process of geometric image calibration, and so that the shortcomings of the conventional calibration phantom in failing to fit the dual-axis scan imaging system could be substantially overcome.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
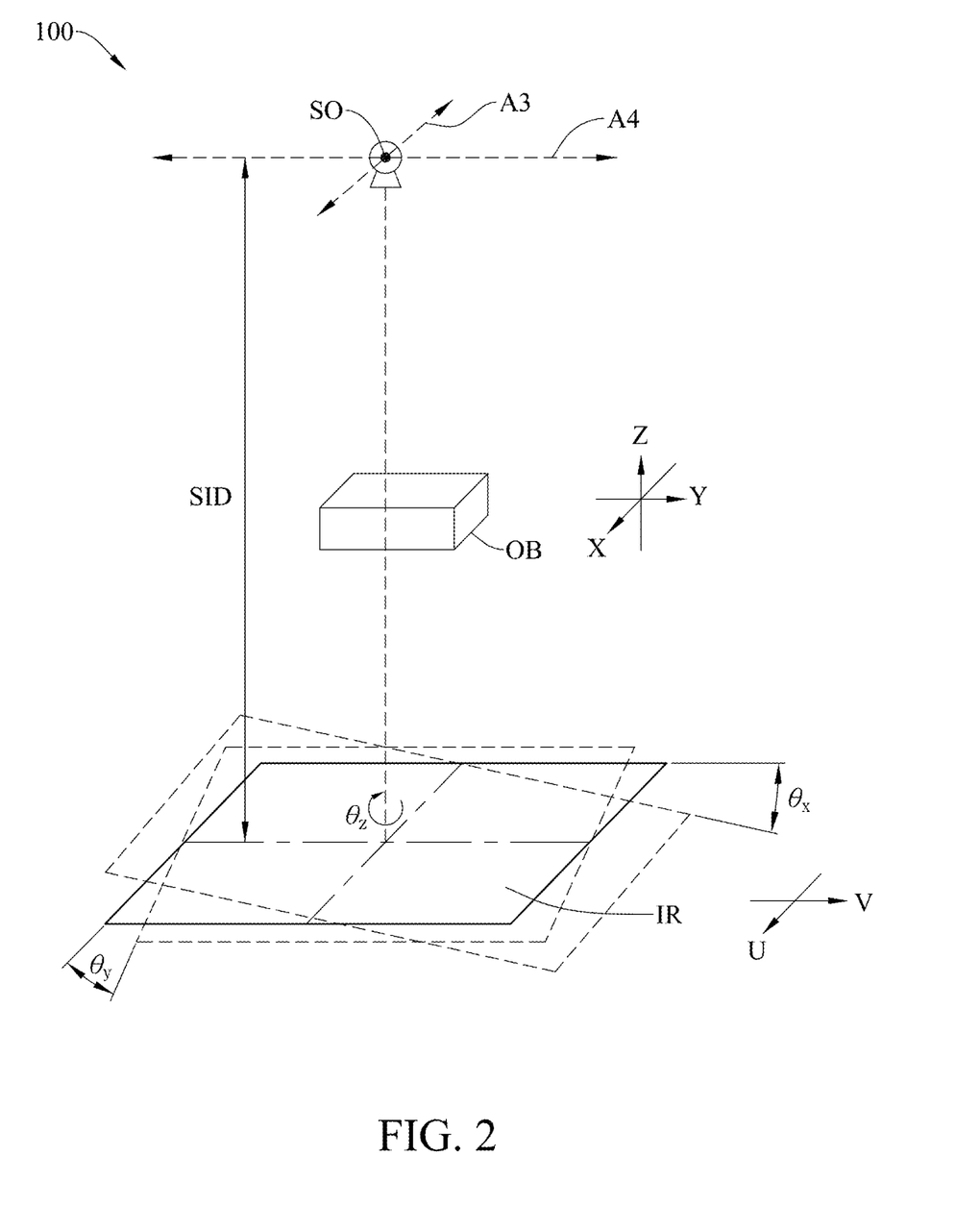
FIG. 2 is a schematic view of an embodiment of the geometric calibration system for dual-axis digital tomosynthesis in accordance with this disclosure.

Referring to FIG. 2, an embodiment of the geometric calibration system for dual-axis digital tomosynthesis is schematically shown. The geometric calibration system for dual-axis digital tomosynthesis 100 includes a light source SO, a geometric calibration phantom OB and a planar detector IR. The geometric calibration phantom OB (defined with a 3D coordinate system X-Y-Z) is located between the light source SO and the planar detector IR (defined with a 2D coordinate system U-V). The light source SO, used for emitting X-ray, can perform scans along an H-F directional scan axis A3 and an L-R directional scan axis A4.

Figure 3:
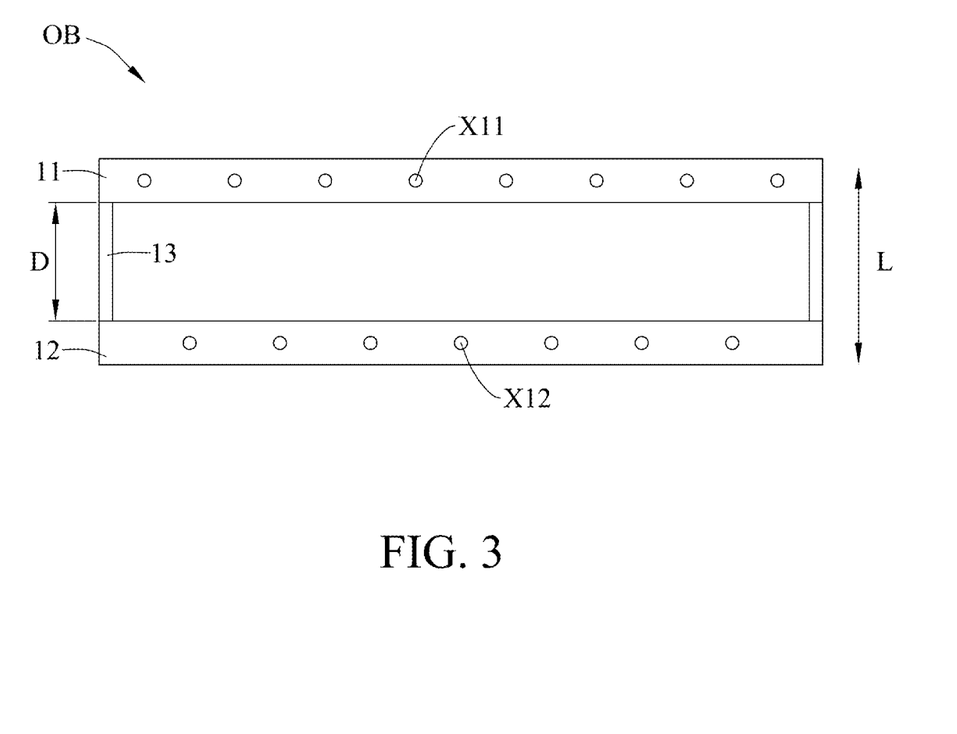
FIG. 3 shows schematically an exemplary example of the geometric calibration phantom in accordance with this disclosure.

As shown in FIG. 3, the geometric calibration phantom OB includes a first plate 11, a second plate 12 and a plurality of mark points X11, X12. In this embodiment, the first plate 11 and the second plate 12 can be acrylic plates, and the first plate 11 and the second plate 12 are connected by a connection member 13 so as to keep a depth distance D in a depth direction L between the first plate 11 and the second plate 12. The first plate 11 is furnished with a plurality of mark points X11, and the second plate 12 is furnished with a plurality of mark points X12, in which the mark points X11, X12 can made of steel or any high-attenuating metal with respect to X-ray. In addition, along a coordinate axis extending in the depth direction L, a coordinate position of any of the mark points X11 on the first plate 11 is never coincided or collinear with that of another mark point X12 on the second plate 12, but distributed in an interlacing manner. Under such an arrangement, in an X-ray projection of dual-axis scanning, possible overlapping of any two projected points of the mark points X11, X12 on the planar detector IR can be avoided.

Figure 4:
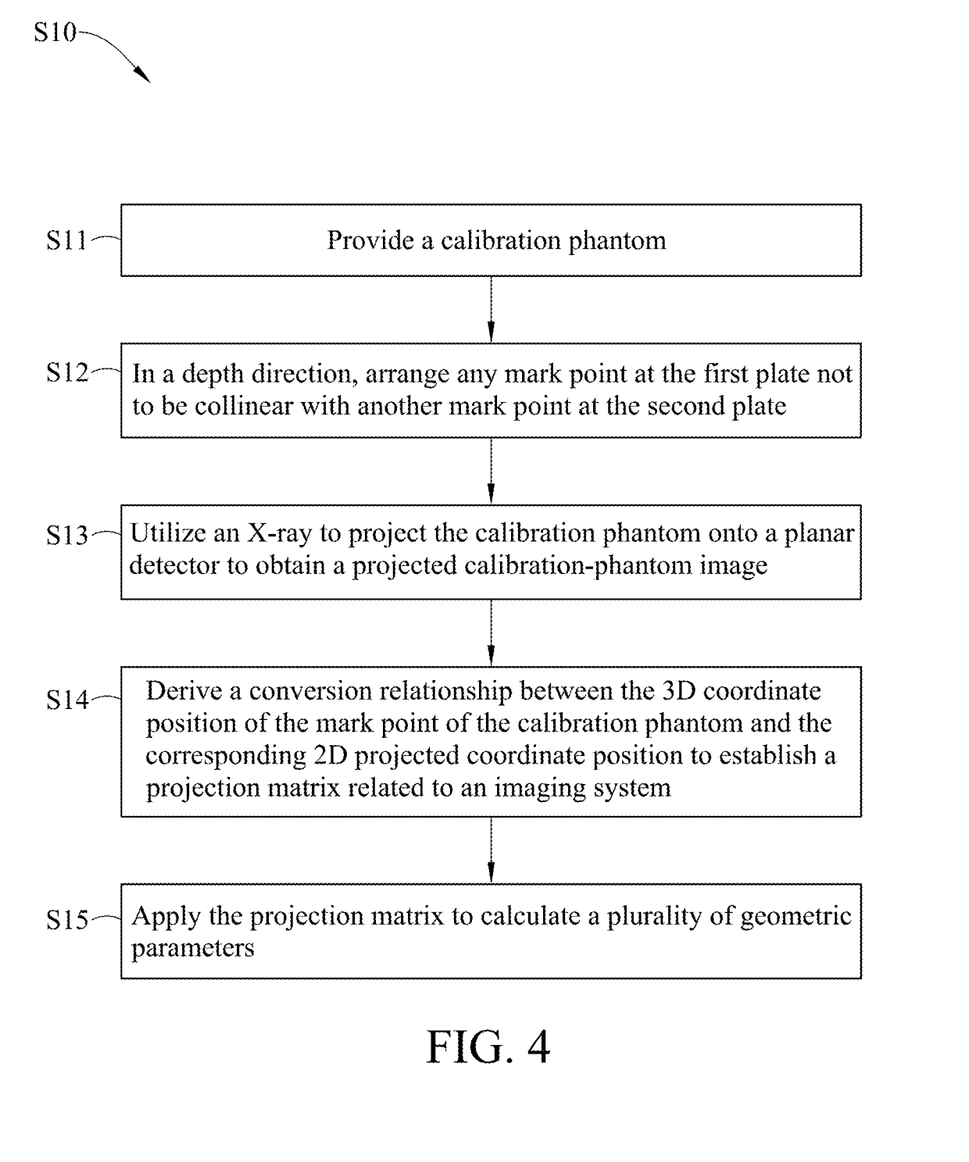
FIG. 4 is s flowchart of an embodiment of the geometric calibration method for dual-axis digital tomosynthesis in accordance with this disclosure.

Refer to FIG. 1 through FIG. 4, in which FIG. 4 is a flowchart of an embodiment of the geometric calibration method for dual-axis digital tomosynthesis in accordance with this disclosure. As shown, the geometric calibration method for dual-axis digital tomosynthesis S10 includes Step S11 to Step S15 as follows. In performing Step S11, the geometric calibration phantom OB is provided, in which the geometric calibration phantom OB includes the first plate 11, the second plate 12 and a plurality of mark points X11, X12. Perpendicular to the depth direction L, the first plate 11 furnished with the mark points X11 and the second plate 12 furnished with the mark points X 12 are spaced by the depth distance D. Thereupon, each of the mark points X11, X12 inside the geometric calibration phantom OB has a corresponding 3D coordinate position (x, y, z). Then, in performing Step S12, along a coordinate axis extending in the depth direction L, a coordinate position of any of the mark points X11 on the first plate 11 is never collinear with that of another mark point X12 on the second plate 12, but distributed in an interlacing manner between the mark points X11 and the mark points X12.

Then, in performing Step S13, the X-ray is introduced to project the geometric calibration phantom OB onto the planar detector IR so as to obtain a corresponding projected image of the calibration phantom OB. In detail, to project the geometric calibration phantom OB onto the planar detector IR, the light source SO is used to emit the X-ray for projecting the geometric calibration phantom OB so as to obtain a projected calibration-phantom image on the planar detector IR. In the process of projecting an image of the geometric calibration phantom OB onto the planar detector IR though radiation of the X-ray, following steps are executed. Firstly, centroids at the projected calibration-phantom image on the planar detector IR with respect to individual mark points X11, X12 are calculated, such that respective 2D projected coordinate positions for individual mark points on the 2D coordinate system U-V can be derived. Namely, each of the mark points X11, X12 is projected into the projected calibration-phantom image, and then centroids on the projected calibration-phantom image with respect to the corresponding mark points can be located to determine the respective 2D projected coordinate positions (u, v) of corresponding centroids for individual mark point X11, X12 can be obtained. In one exemplary example of this disclosure, image preprocessing for precisely and rapidly acquiring the 2D projected coordinate positions of the mark points X11, X12 can be performed upon the projected calibration-phantom image of the geometric calibration phantom OB. The image preprocessing can include image smoothing, image thresholding and the like image-processing technique.

In this embodiment, the X-ray is used to project the geometric calibration phantom OB to the planar detector IR. Since the planar detector IR of this embodiment is formed as a 2D plane, thus the 3D coordinate position (x, y, z) of each of the mark points X11, X12 in the geometric calibration phantom OB can be mapped to a corresponding 2D projected coordinate position (u, v) on the planar detector IR. Then, in performing Step S14, by realizing conversion relationships between the 3D coordinate positions (x, y, z) of the individual mark points X11, X12 and the corresponding 2D projected coordinate position (u, v), a projection matrix equation for the aforesaid imaging system can be expressed by equation (1) as follows:

$$w[u,v,1]^T = P[x,y,z,1]^T \qquad (1)$$

In equation (1), the projection matrix P is a 3×4 projection matrix, w is a dimensionless distance weighting factor to match the 3D coordinate system (X, Y, Z) and the projected 2D coordinate system (U,V) for the mark points, and T is a transpose symbol. Since the mark points X11, X12 are preset points at the geometric calibration phantom OB, thus the 3D coordinate positions (x, y, z) of individual mark points X11, X12 at the geometric calibration phantom OB are already known. As the geometric calibration phantom OB is projected onto the planar detector IR via radiating the X-ray, the 2D projected coordinate positions (u, v) on the planar detector IR with respect to individual mark points X11, X12 can then be derived after the respective centroid coordinates are calculated. Thus, with equation (1) to derive the projection matrix P, and since the 3D coordinate position of any of the mark points X11 on the first plate 11 is coincided or collinear with none of the 3D coordinate position of any mark point X12 on the second plate 12 as shown in FIG. 3, thus, during the dual-axis tomosynthesis upon the mark points X11, X12, possible overlapping of the projected images on the planar detector IR with respect to any two mark points X11, X12 at the first plate 11 and the mark point X12, respectively, can be avoided.

Hence, from equation (1), by giving the 3D coordinate positions (x, y, z) of the mark points X11, X12 in the geometric calibration phantom OB, and the 2D projected coordinate positions (u, v) on the planar detector IR with respect to the mark points X11, X12, then the projection matrix P can be calculated. Then, in performing Step S15, the projection matrix P is utilized to derive a plurality of geometric parameters. In addition, the projection matrix P can be decomposed into the following equation (2):

$$P = K[R][t] \qquad (2)$$

In equation (2), K is a 3×3 intrinsic matrix, R is a 3×3 rotation matrix, and t is a 3×1 translation vector. The intrinsic matrix K can be expressed by equation (3) as follows:

$$K = \begin{pmatrix} \frac{SID}{P_u} & 0 & u_0 \\ 0 & \frac{SID}{P_v} & v_0 \\ 0 & 0 & 1 \end{pmatrix} \qquad (3)$$

In equation (3), SID is a projection distance from the light source SO to a surface of the planar detector IR as shown in FIG. 2, $P_u$ and $P_v$ are pixel's height and width of the planar detector IR, and $u_0$ and $v_0$ are coordinates in the directions u and v, respectively, for the point on the planar detector IR with respect to a center light beam emitted vertical down from the light source SO.

In equation (2), the rotation matrix R can be expressed by equation (4) as follows:

$$R = \begin{bmatrix} \cos\theta_z\cos\theta_y & \begin{matrix}-\sin\theta_z\cos\theta_x + \\ \cos\theta_z\sin\theta_y\sin\theta_x\end{matrix} & \begin{matrix}\sin\theta_z\sin\theta_x + \\ \cos\theta_z\sin\theta_y\cos\theta_x\end{matrix} \\ \sin\theta_z\cos\theta_y & \begin{matrix}\cos\theta_z\cos\theta_x + \\ \sin\theta_z\sin\theta_y\sin\theta_x\end{matrix} & \begin{matrix}-\cos\theta_z\cos\theta_x + \\ \sin\theta_z\sin\theta_y\cos\theta_x\end{matrix} \\ -\sin\theta_y & \cos\theta_y\sin\theta_x & \cos\theta_y\cos\theta_x \end{bmatrix} \qquad (4)$$

In equation (4), Euler angles ($\theta_x$, $\theta_y$, $\theta_z$) stand for inclination angles of the planar detector IR with respect to the coordinate system X-Y-Z defined with the geometric calibration phantom OB.

In equation (2), the translation vector t can be expressed by equation (5) as follows:

$$t = [t_x, t_y, t_z]^T \qquad (5)$$

In equation (5), $t_x$, $t_y$, $t_z$ stand for deviations between the coordinate system defined with the geometric calibration phantom OB and that defined with the light source SO.

In step S14, in order to improve calculation accuracy in deriving the projection matrix P, following steps can be included. Firstly, with the calculated projection matrix P and the 3D coordinate positions (x, y, z) of all individual mark points X11, X12, equation (1) is applied to estimate corresponding coordinate positions ($u_i(P)$, $v_i(P)$) of the respective mark points. Then, apply a nonlinear least squares method to reduce the difference between the 2D projected coordinate position ($u_i(P)$, $v_i(P)$) of one specific mark point calculated from the projection matrix and the corresponding 2D projected coordinate position ($u_i$, $v_i$) of the same mark point calculated from the projected image. By applying the nonlinear least squares method, regressive process is utilized to narrow the aforesaid difference and thus to converge the calculated projection matrix P into an optimal projection matrix P. Preferably, the aforesaid process can be a Levenberg-Marquradt algorithm, and an objective function can be defined as equation (6) as follows:

$$E = \sum_{i=1}^{N} [(u_i - u_i(P))^2 + (v_i - v_i(P))^2] \qquad (6)$$

In equation (6), $(u_i, v_i)$ is the 2D projected coordinate position of one of the mark points X11, X12, $(u_i(P), v_i(P))$ is the projected coordinate position of the same mark point calculated through the projection matrix P, and N is the number of the mark points X11, X12. The initial value for this regressive calculation can be the calculated projection matrix P through equation (1) by applying the direct linear transformation (DLT) method.

As described above, the projection matrix P, the intrinsic matrix K and the rotation matrix R of this embodiment can be obtained through the aforesaid calculations, and, on the other hand, the geometric parameters of the imaging system can be derived by the following equations. Firstly, the coordinate $(u_0, y_0)$ in the corresponding directions u and v on the planar detector IR with respect to the center light beam vertical down from the light source SO can be derived by the intrinsic matrix K in equation (3). For example, $$u_0 = K_{13}, v_0 = K_{23} \quad (7)$$

Then, the SID from the light source SO to the detector IR can be also derived from the intrinsic matrix K of equation (3). For example, $$SID = K_{11} P_u = K_{22} P_v \quad (8)$$

In addition, the rotational inclination angles ($\theta x$, $\theta y$, $\theta z$) of the planar detector IR with respect to the coordinate system X-Y-Z defined at the geometric calibration phantom OB can be derived by the rotation matrix of equation (4). For example, $$\theta_x \arctan(R_{32}, R_{33}) \quad (9)$$

$$\theta_y = \arctan(-R_{31}) \quad (10)$$

$$\theta_z = \arctan(R_{21}, R_{11}) \quad (11)$$

Finally, the 3D coordinate position $S = [S_x, S_y, S_z, 1]^T$ of the light source SO can be derived by applying the projection matrix P and the following limitation in equation (12).

$$PS = 0 \quad (12)$$

Thereupon, according to the aforesaid methods provided in this disclosure, a set of geometric parameters can be obtained by utilizing the projected calibration-phantom image through one-step imaging. In this embodiment, the geometric parameters include the deviation $(u_0, v_0)$ of the center light beam vertical down from the light source SO to aim at a center of the planar detector IR, the SID from the light source SO to the planar detector IR, the inclination angles ($\theta_x$, $\theta_y$, $\theta_z$) of the planar detector IR and the position $(S_x, S_y, S_z)$ of the light source SO.

Figure 5A:
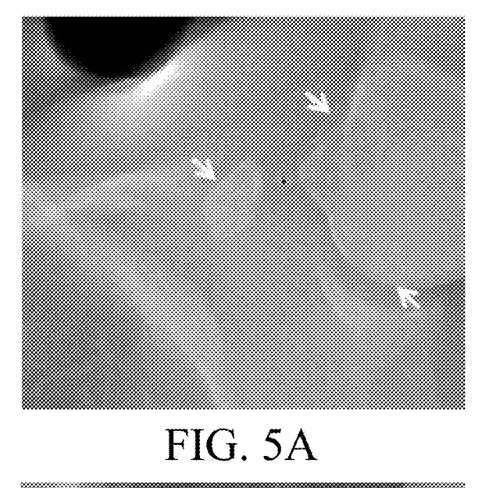
FIG. 5A demonstrates schematically a reconstructed image around rims of a scapula by a conventional dual-axis chest DTS system.
Figure 5B:
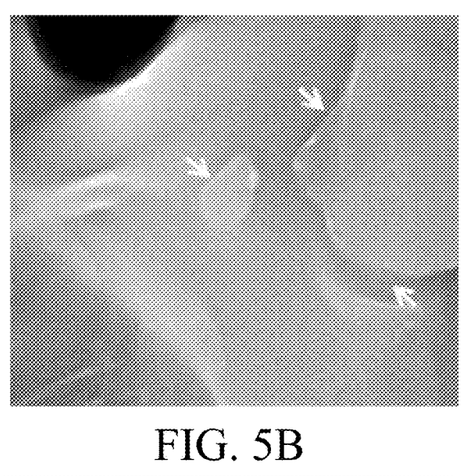
FIG. 5B demonstrates schematically a reconstructed image around rims of the scapula by applying the geometric calibration method for the dual-axis chest DTS in accordance with this disclosure.
Figure 5C:
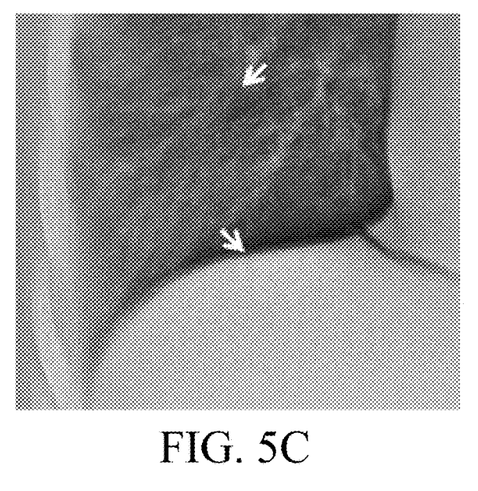
FIG. 5C demonstrates schematically a reconstructed image at a boundary of a diaphragm by the conventional dual-axis chest DTS system.
Figure 5D:
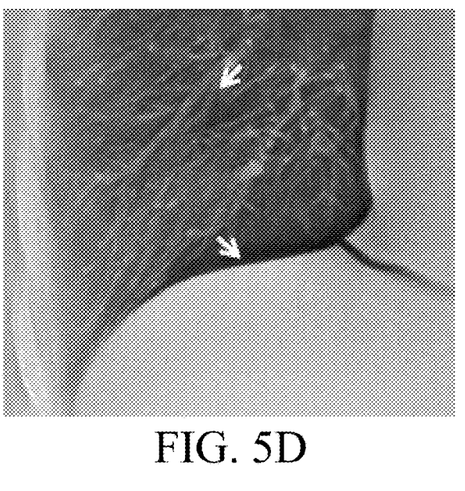
FIG. 5D demonstrates schematically a reconstructed image at the boundary of the diaphragm by applying the geometric calibration method for the dual-axis chest DTS in accordance with this disclosure.

By utilizing the geometric parameters obtained by the aforesaid processes, an entire scan track of the dual-axis scan-geometry tomosynthesis system can be sketched and thus used for evaluating geometric misalignments such as whether or not the two center points of the respective axes (i.e., the H-F directional scan axis and the L-R directional scan axis) are coincided, and whether or not the inclination angle between these two axes is excessive. In this embodiment, the inclination angle is generated due to an ill match of the center point of the H-F directional scan axis A1 and the center point of the L-R directional scan axis A2. For example, by giving (1) the H-F directional scan axis a scan stroke from −300 mm to +300 mm for capturing 61 projected images and (2) the L-R directional scan axis another scan stroke from −150 mm to +150 mm for capturing 31 projected images, if center points of different kinematic axes in the dual-axis scan are not coincided, then artifact would appear in the reconstructed image. In the case that any geometric misalignment of the kinematic mechanism exceeds an allowable range, the geometric parameters can be fed back to the image-reconstructing algorithm so as to correct the geometric matrix of the system. After several feedback and corrections, the reconstructed image can be well calibrated, so that a quality reconstructed image can be obtained. For example, obvious phenomena of fuzzy dislocations at the rims of scapula in FIG. 5A and the boundary of diaphragm in FIG. 5C can be visually observed, particularly in which an image of a pulmonary vessel as indicated by an arrow in FIG. 5C is vague. However, after the geometric parameters realized in this embodiment are applied into the image-reconstructing algorithm to correct the geometric matrix of the system, then the corresponding reconstructed images obtained through geometric calibrations provided by the dual-axis chest tomosynthesis according to this disclosure as shown in FIG. 5B and FIG. 5D can be obtained. From these two reconstructed images, significant imaging improvements can be easily observed. Thereupon, more medical supports can be provided to promote accuracy in disease diagnosis, and thus to enhance quality of medications.

In summary, by providing the geometric calibration method and system applicable for the digital tomosynthesis system with dual-axis scan geometry according to this disclosure, the aforesaid shortcoming that the conventional geometric calibration method and apparatus cannot be applied to the imaging system with the dual-axis scan geometry can be substantially resolved. In this disclosure, the geometric calibration method applies basically the projection matrix to utilize position relationships between the calibration-phantom mark points and the corresponding projected mark points to derive the geometric parameters sufficient for representing the digital tomosynthesis system with the dual-axis digital scan geometry.

In addition, in the geometric calibration phantom provided by this disclosure, the arrangement of the mark points at the first and second plates are specifically designed and optimized, such that the digital tomosynthesis system with the dual-axis scan geometry in accordance with this disclosure can resolve the problems in overlapping the related mark points during the process of geometric image calibration, and so that the shortcomings of the conventional calibration phantom in failing to fit the dual-axis scan imaging system could be substantially overcome.

Finally, besides being applicable for the digital dual-axis scan tomosynthesis system, the method and system provided by this disclosure can be also applied to the conventional single-axis scan imaging system, computed tomography system, and the other 3D limited angle scan systems, for reducing geometric misalignments of the system, removing artifacts, and improving imaging quality.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A geometric calibration method for dual-axis digital tomosynthesis, comprising the steps of:
    (a) providing a calibration phantom, wherein the calibration phantom includes a first plate, a second plate and a plurality of mark points, the first plate and the second plate are spaced by a depth distance in a depth direction, and the plurality of mark points is distributed to the first plate and the second plate;

(b) in the depth direction, arranging a 3D coordinate position of any of the plurality of mark points at the first plate not to be collinear with another 3D coordinate position of another one of the plurality of mark points at the second plate;

(c) utilizing an X-ray to project the calibration phantom onto a planar detector, so as to obtain a projected calibration-phantom image, wherein the 3D coordinate position of each of the plurality of mark points disposed at the first plate and the second plate is in correspondence to a 2D projected coordinate position at the planar detector;

(d) deriving a conversion relationship between the 3D coordinate position of each of the plurality of mark points disposed at the first plate and the second plate and the corresponding 2D projected coordinate position to establish a projection matrix related to an imaging system; and (e) applying the projection matrix to calculate a plurality of geometric parameters.

2. The geometric calibration method for dual-axis digital tomosynthesis of claim 1, wherein the step (c) includes a step of calculating a centroid in the projected calibration-phantom image with respect to each of the plurality of mark points so as to obtain the corresponding 2D projected coordinate position.

3. The geometric calibration method for dual-axis digital tomosynthesis of claim 1, after the step (e), further including a step of judging the plurality of geometric parameters to evaluate whether or not a geometric misalignment exists between an H-F directional scan axis and an L-R directional scan axis of a digital tomosynthesis system with dual-axis scan geometry, and further applying the plurality of geometric parameters into an image-reconstructing algorithm so as to calibrate a reconstructed image, wherein the geometric misalignment is to determine whether or not a center position of the H-F directional scan axis and another center position of the L-R directional scan axis is coincided, or whether or not an inclination angle between the H-F directional scan axis and the L-R directional scan axis is excessive.

4. The geometric calibration method for dual-axis digital tomosynthesis of claim 1, after the step (e), further including the steps of:

(d1) utilizing the projection matrix and the 3D coordinate position of each of the plurality of mark points to derive a coordinate position; and (d2) applying a nonlinear least squares method to reduce a difference between the coordinate position and the corresponding 2D projected coordinate position of the same mark point in the projected calibration-phantom image.

5. A geometric calibration system for dual-axis digital tomosynthesis, comprising:

a planar detector;

a light source for emitting an X-ray; and a geometric calibration phantom, including a first plate, a second plate and a plurality of mark points;

wherein the first plate and the second plate are spaced by a depth distance in a depth direction, the plurality of mark points is distributed to the first plate and the second plate, and, in the depth direction, a 3D coordinate position of any of the plurality of mark points at the first plate is not collinear with another 3D coordinate position of another one of the plurality of mark points at the second plate;

wherein the calibration phantom is projected onto the planar detector via the X-ray to obtain a projected calibration-phantom image, and the 3D coordinate position of each of the plurality of mark points disposed at the first plate and the second plate is in correspondence to a 2D projected coordinate position at the planar detector;

where a conversion relationship between the 3D coordinate position of each of the plurality of mark points disposed at the first plate and the second plate and the corresponding 2D projected coordinate position is derived to establish a projection matrix related to an imaging system;

wherein the projection matrix is applied to calculate a plurality of geometric parameters.

* * * * *